United States Patent [19]

Ardman

[11] Patent Number: 5,252,556
[45] Date of Patent: Oct. 12, 1993

[54] FRAGMENT CAPABLE OF BINDING ANTI-CD43 AUTOANTIBODIES

[75] Inventor: Blair Ardman, Brookline, Mass.

[73] Assignee: New England Medical Center Hospitals, Inc., Boston, Mass.

[21] Appl. No.: 503,458

[22] Filed: Mar. 30, 1990

[51] Int. Cl.[5] ............................................. A61K 39/00
[52] U.S. Cl. ............................................. 514/8; 424/88; 530/350; 530/395; 435/69.1; 435/69.3
[58] Field of Search ................ 435/5, 7.1, 69.1, 69.3; 530/380, 350, 395; 424/88; 514/8

[56] References Cited

U.S. PATENT DOCUMENTS 4,853,326 8/1989 Quash ........................................ 435/5

OTHER PUBLICATIONS

Schimpf et al., Clin. exp. Immunol. 75:178–183, 1989.
Ozturk et al., Journal of Clinical Immunology 7:130–139, 1987.
Stricker et al., Nature 327:710–713, 1987.
Kloster et al., Clinical Immunology and Immunopathology 30:330–335, 1984.
Pollack et al., Antibodies to Non-HLA Antigens in AIDS 209–213, 1983.
Dorsett et al., The American Journal of Medicine 78:621–625, 1985.
Pruzanski et al., AIDS Research 1:211–220, 1984.
Kirpov et al., N. Engl. J. Med. 312:1517, 1985.
Tomar et al., Clinical Immunology and Immunopathology 37:37–47, 1985.
Kiprov et al., Acquired Immune Deficiency Syndrome 299–308, 1984.
Chams et al., AIDS 2:353–362, 1988.
Kowalski et al., Proc. Natl. Acad. Sci. USA 86:3346–3350, 1989.
Thiriart et al., AIDS 2:345–351, 1988.
Karpatkin et al., Proc. Natl. Acad. Sci. USA 85:9763–9767, 1988.
Remold-O'Donnell et al., Blood 70:104–109, 1987.

*Primary Examiner*—Christine M. Nucker
*Assistant Examiner*—Jeffrey Stucker
*Attorney, Agent, or Firm*—Fish & Richardson

[57] ABSTRACT

A fragment capable of binding to an anti-CD43 autoantibody made by a human infected with HIV-1. The fragment, which includes a part or the entirety of an amino acid sequence corresponding to positions 20-254 of CD43, can be used in treatment or diagnosis of HIV-1 infections.

5 Claims, 7 Drawing Sheets

```
Met Ala Thr Leu Leu Leu Leu Leu Gly Val Leu Val Val Ser Pro Asp Ala
ATG GCC ACG CTT CTC CTT CTC CTT GGG GTG CTG GTG GTA AGC CCA GAC GCT

Leu Gly Ser Thr Thr Ala Val Gln Thr Pro Thr Ser Gly Glu Pro Leu Val
CTG GGG AGC ACA ACA GCA GTG CAG ACA CCC ACC TCC GGA GAG CCT TTG GTC
                         167

Ser Thr Ser Glu Pro Leu Ser Ser Lys Met Tyr Thr Thr Ser Ile Thr Ser
TCT ACT AGC GAG CCC CTG AGC TCA AAG ATG TAC ACC ACT TCA ATA ACA AGT
                                                            242

Asp Pro Lys Ala Asp Ser Thr Gly Asp Gln Thr Ser Ala Leu Pro Pro Ser
GAC CCT AAG GCC GAC AGC ACT GGG GAC CAG ACC TCA GCC CTA CCT CCC TCA

Thr Ser Ile Asn Glu Gly Ser Pro Leu Trp Thr Ser Ile Gly Ala Ser Thr
ACT TCC ATC AAT GAG GGA TCC CCT CTT TGG ACT TCC ATT GGT GCC AGC ACT
                         317

Gly Ser Pro Leu Pro Glu Pro Thr Thr Tyr Gln Glu Val Ser Ile Lys Met
GGT TCC CCT TTA CCT GAG CCA ACA ACC TAC CAG GAA GTT TCC ATC AAG ATG
                                                            392

Ser Ser Val Pro Gln Glu Thr Pro His Ala Thr Ser His Pro Ala Val Pro
TCA TCA GTG CCC CAG GAA ACC CCT CAT GCA ACC AGT CAT CCT GCT GTT CCC

Ile Thr Ala Asn Ser Leu Gly Ser His Thr Val Thr Gly Gly Thr Ile Thr
ATA ACA GCA AAC TCT CTA GGA TCC CAC ACC GTG ACA GGT GGA ACC ATA ACA
                         467

Thr Asn Ser Pro Glu Thr Ser Ser Arg Thr Ser Gly Ala Pro Val Thr Thr
ACG AAC TCT CCA GAA ACC TCC AGT AGG ACC AGT GGA GCC CCT GTT ACC ACG
                                                            542

Ala Ala Ser Ser Leu Glu Thr Ser Arg Gly Thr Ser Gly Pro Pro Leu Thr
GCA GCT AGC TCT CTG GAG ACC TCC AGA GGC ACC TCT GGA CCC CCT CTT ACC
                617

Met Ala Thr Val Ser Leu Glu Thr Ser Lys Gly Thr Ser Gly Pro Pro Val
ATG GCA ACT GTC TCT CTG GAG ACT TCC AAA GGC ACC TCT GGA CCC CCT GTT

Thr Met Ala Thr Asp Ser Leu Glu Thr Ser Thr Gly Thr Thr Gly Pro Pro
ACC ATG GCA ACT GAC TCT CTG GAG ACC TCC ACT GGG ACC ACT GGA CCC CCT
                                                        692

Val Thr Met Thr Thr Gly Ser Leu Glu Pro Ser Ser Gly Ala Ser Gly Pro
GTT ACC ATG ACA ACT GGC TCT CTG GAG CCC TCC AGC GGG GCC AGT GGA CCC

Gln Val Ser Ser Val Lys Leu Ser Thr Met Met Ser Pro Thr Thr Ser Thr
CAG GTC TCT AGC GTA AAA CTA TCT ACA ATG ATG TCT CCA ACG ACC TCC ACC
                767

Asn Ala Ser Thr Val Pro Phe Arg Asn Pro Asp Glu Asn Ser Arg Gly Met
AAC GCA AGC ACT GTG CCC TTC CGG AAC CCA GAT GAG AAC TCA CGA GGC ATG
                                                        842

Leu Pro Val Ala Val Leu Val Ala Leu Leu Ala Val Ile Val Leu Val Ala
CTG CCA GTG GCT GTG CTT GTG GCC CTG CTG GCG GTC ATA GTC CTC GTG GCT

Leu Leu Leu Leu Trp Arg Arg Arg Gln Lys Arg Arg Thr Gly Ala Leu Val
CTG CTC CTG CTG TGG CGC CGG CGG CAG AAG CGG CGG ACT GGG GCC CTC GTG
            917

Leu Ser Arg Gly Gly Lys Arg Asn Gly Val Val Asp Ala Trp Ala Gly Pro
CTG AGC AGA GGT GGC AAG CGT AAC GGG GTG GTG GAC GCC TGG GCT GGG CCA
                                                    992
```

FIG. 13A

```
Ala Gln Val Pro Glu Glu Gly Ala Val Thr Val Thr Val Gly Gly Ser Gly
GCC CAG GTC CCT GAG GAG GGG GCC GTG ACA GTG ACC GTG GGA GGG TCC GGG

Gly Asp Lys Gly Ser Gly Phe Pro Asp Gly Glu Gly Ser Ser Arg Arg Pro
GGC GAC AAG GGC TCT GGG TTC CCC GAT GGG GAG GGG TCT AGC CGT CGG CCC
    1067

Thr Leu Thr Thr Phe Phe Gly Arg Arg Lys Ser Arg Gln Gly Ser Leu Ala
ACG CTC ACC ACC TTC TTT GGC AGA AGA AAG TCT GCG CAG GGC TCC CTG GCG
                                    1142

Met Glu Glu Leu Lys Ser Gly Ser Gly Pro Ser Leu Lys Gly Glu Glu Glu
ATG GAG GAG CTG AAG TCT GGG TCA GGC CCC AGC CTC AAA GGG GAG GAG GAG

Pro Leu Val Ala Ser Glu Asp Gly Ala Val Asp Ala Pro Ala Pro Asp Glu
CCA CTG GTG GCC AGT GAG GAT GGG GCT GTG GAC GCC CCA GCT CCT GAT GAG
1217

Pro Glu Gly Gly Asp Gly Ala Ala Pro
CCC GAA GGG GGA GAC GGG GCT GCC CCT
                                1292
```

FIG. 13B

FRAGMENT CAPABLE OF BINDING ANTI-CD43 AUTOANTIBODIES

BACKGROUND OF THE INVENTION

This invention was made with Government support under Grant No. AI 27729 awarded by the National Institutes of Health. The Government has certain rights in the invention.

This invention relates to the diagnosis and treatment of HIV-1 infections.

Human immunodeficiency virus type 1 (HIV-1) is the etiologic agent of acquired immunodeficiency syndrome (AIDS), Broder et al. (1984) N. Engl. J. Med. 311:1292-1297 and Barre-Sinoussi et al. (1983) Science 220:868-870. Depletion of the CD4+ lymphocyte population is believed to account for most of the severe immunologic abnormalities seen in AIDS patients, Fauci et al. (1984) Ann. Int. Med. 100:92-106. Depletion occurs prior to, or coincident with, development of the severe opportunistic infections seen in most HIV-1-infected individuals, Gottlieb et al. (1981) N. Eng. J. Med. 305:1425-1431, Lane et al. (1985) Am. J. Med. 78:417-422, and Friedman-Kien et al. (1982) Ann. Int. Med. 96:693-699.

Antibodies that react with allogenic T lymphocytes have been detected in the serum of HIV-1 seropositive individuals, Pollack et al. (1983) in Non-HLA Antigens in Health, Aging, and Malignancy, (Alan R. Liss, New York) pp. 209-213, Kloster et al. (1984) Clin. Immunol. Immunopath 30:330-335, Pruzanski et al. (1984) Aids Res. 1:211-220, Kiprov et al. (1985) N. Engl. J. Med. 312:1517, Dorsett et al. (1985) Am. J. Med. 78:621-626, Tomar et al. (1985) Clin. Immunol. Immunopath 37:37-47, Stricker et al. (1987) Nature 327:710-713, and Otzurk et al. (1987) J. Clin. Immunol. 7:130-139. Recently, serum antibodies that bind to soluble, recombinant forms of the cell surface protein CD4 were detected in 9-13% of individuals infected by HIV-1, Chams et al. (1988) AIDS 2:353-361, Thiriart et al. (1988) AIDS 2:345-351, and Kowalski et al. (1989) Proc. Natl. Acad. Sci. USA 86:3346-3350, but the ability of such antibodies to bind to native CD4 could not be demonstrated, Chams et al. (1988), AIDS 2:353-361.

CD43, also known as leukosialin, sialophorin, gpL115, and LSCP, is a major lymphocyte surface sialoglycoprotein expressed by essentially all leukocytes, Borche et al. (1987) Eur. J. Immunol. 17:1523-1526. The binding of antibodies to CD43 can activate T lymphocytes, Mentzer et al (1987) S. Exp. Med. 165:1383-1392, Axelsson (1988) J. Immunol. 141:2912-2917, bypassing the T cell receptor/CD3 complex, Silverman et al. (1989) J. Immunol. 142:4194-4200. CD43 expression is diminished or abnormal on lymphocytes from children with Wiskott Aldrich syndrome, a severe X chromosome-linked immunodeficiency, Remold-O'Donnell et al. (1984) J. Exp. Med. 159:1705-1723. A CD43-like molecule has been found on the surface of brain cells in rats, Losy et al. (1984) J. Neuro cytol. 18:71-76.

SUMMARY OF THE INVENTION

In general, the invention features AIDS therapy using a CD43 antigen (defined as a substance capable of specifically binding to an anti-CD43 autoantibody); useful CD43 antigens include a CD43 fragment, preferably a soluble CD43 fragment, capable of binding to an anti-CD43 autoantibody made by a human infected with HIV-1. A CD43 fragment, as used herein, is a quence of CD43. An autoantibody, as used herein, is an antibody, made by an individual, that binds a cellular component synthesized by that individual. Soluble, as used herein, means soluble in an aqueous biological fluid, e.g., blood. The fragment contains none of the hydrophobic transmembrane portion of CD43, or only a portion of the transmembrane portion which does not prevent solubilization of the fragment. The fragment is large enough (generally, at least 15-20 amino acid residues) to effectively bind anti-CD43 autoantibody. The fragment need not have perfect homology with the corresponding region of naturally occurring CD43, but has sufficient homology to bind to an anti-CD43 autoantibody. A DNA sequence encoding the fragment can be inserted into an expression vector and that construction can be introduced into a cell for expression of the recombinant polypeptide.

The CD43 antigen of the invention (soluble CD43 fragment or any other soluble CD43 antigen, e.g., a saccharide that binds an anti-CD43 autoantibody) can be administered to a human patient infected with HIV-1, to bind anti-CD43 autoantibodies produced by the patient and thereby prevent them from deleteriously binding to CD43+ lymphocytes. Binding of anti-CD43 autoantibodies to lymphocytes is believed to contribute to the course of disease in AIDS patients by, inter alia, marking the CD43+ lymphocytes for removal from circulation by the spleen. Administration of a CD43 antigen, e.g., a soluble CD43 fragment may also compete with other cell types, e.g., brain cells, for binding to anti-CD43 autoantibodies and thereby protect those cells from the deleterious effects of anti-CD43 autoantibody binding. In preferred embodiments the soluble CD43 fragment is less glycosylated than is the corresponding segment of a CD43 molecule isolated from the peripheral lymphocytes of an individual who is not infected with HIV 1.

A level of glycosylation that allows binding can be achieved by a number of conventional methods, e.g., by expressing the soluble CD43 fragment in an expression system that does not normally fully glycosylate foreign proteins, by expressing the soluble CD43 fragment in an expression system in which normal glycosylation is impaired, e.g., by the addition of an inhibitor, or by the enzymatic removal of sugar residues from a glycosylated soluble CD43 fragment. Sialic acid may be removed enzymatically, e.g., with neuraminadase (acylneuraminyl hydrolase, EC 3.2.1.18), e.g., neuraminadase from Vibrio cholerae which hydrolizes $\alpha$-2,3, $\alpha$-2,4, $\alpha$-2,6, and $\alpha$-2,8 linked terminal sialic acid residues.

Neuraminidase removes sialic acid. The removal of sialic acid (which is highly negatively charged) results in an increase in apparent molecular weights as determined by sodium dodecyl sulfate polyacrylamide gel electrophoresis (SDS-PAGE). Neuraminidase treatment under conditions that result in an increase in apparent molecular weight, as determined by SDS-PAGE, of CD43 isolated from mature lymphocytes from HIV-1 negative individuals of between 5 and 20 kilodaltons (kD), and more preferably of 10 kD, results in a CD43 fragment that binds to anti-CD43 autoantibodies. In preferred embodiments the degree of glycosylation on the soluble CD43 fragment is equivalent to the degree of glycosylation that is found on the corresponding portion of CD43 molecules isolated from normal thymocytes, SupTl cells, or Ig+ lymphocytes from HIV-1 infected individuals. Equivalent glycosylation, as used herein, means (1) less glycosylation than found negative individuals, or (2) an amount of glycosylation that allows binding by an anti-CD43 autoantibody.

The invention also features a method of detecting the presence or progress of an HIV-1 infection in a human patient that includes collecting lymphocytes, e.g., T lymphocytes or thymocytes, from the patient and determining if autoantibodies, e.g., anti CD43 autoantibodies, are bound to the lymphocytes.

The invention also features a method of detecting the presence or progress of an HIV-1 infection in a human patient that includes collecting serum from the patient and determining if the serum contains anti-T cell antibodies, e.g., anti CD43 antibodies.

As described in detail below, individuals infected with HIV-1, but not uninfected individuals, possess autoantibodies to T-cell surface molecules, both in their serum and bound to some of their T-lymphocytes. In particular, an autoantibody to CD43 exists in the serum. T-lymphocytes that have an autoantibody bound to them are termed $Ig^+$ T-lymphocytes. The presence of $Ig^+$ T-lymphocytes correlates with $CD4+$ lymphocyte deficiency in asymptomatic HIV-1 infected individuals. The great majority (over 80%) of the individuals with $Ig^+$ T cells have serum autoantibodies that can bind to T cells. Anti-T cell autoantibodies are also present in some (18%) seropositive individuals who lack $Ig^+$ T cells. The anti-CD43 autoantibodies recognize a partially sialylated form of CD43 that is present on normal human thymocytes, but not on normal circulating T-lymphocytes. Thus HIV-1 infection is seen to be accompanied by a significant autoimmune response, with the autoimmune reaction directed at a critical element of the immune system itself, i.e., the lymphocytes.

The molecules and methods of the invention allow the diagnosis of the presence or progress of an HIV-1 infection. The methods are particularly useful in diagnosing the progress of an HIV-1 infection in asymptomatic individuals.

The molecules and methods of the invention also allow for the treatment of an individual infected with HIV-1. One method includes administering a soluble CD43 antigen, e.g. a soluble CD43 fragment, which protects the patient's lymphocytes by binding an anti-CD43 autoantibody which would otherwise be capable of binding to cellular CD43. An individual infected with HIV-1 may also be treated by the administration of hybrid toxin molecules that include a CD43-antigen coupled to a toxin molecule. The hybrid toxin kills cells that produce anti-CD43 auto antibodies and thus reduces the number of anti-CD43 auto antibodies. Anti-CD43 antibody producing cells may also be eliminated by administration of a CD43 antigen (which results in a proliferation of anti-CD43 antigen-producing cells) followed by the administration of treatment that kills dividing cells, e.g., chemotherapy.

Other features and advantages of the invention will be apparent from the following description of a preferred embodiment and from the claims.

DESCRIPTION OF A PREFERRED EMBODIMENT

The drawings are first described.

DRAWINGS

FIGS. 13A and 13B are the sequence of the gene encoding CD43.

Surface $Ig^+$ T Cells

Peripheral blood mononuclear cells from fifty-two HIV-1 seropositive individuals and forty-four HIV-1 seronegative individuals were tested by two color immunofluorescence for the presence of $CD3+$ lymphocytes that had surface bound immunoglobulins (surface $Ig^+$ or $Ig^+$), as described below. Thirty three of the HIV-1 seropositive individuals (63%) had surface $IG+$ T cells in their blood, Table 1. None of the seronegative individuals had $Ig^+$ T cells in their blood.

TABLE 1

RELATIONSHIP OF HIV-1 SEROLOGY TO PRESENCE OF SURFACE $Ig^+$ T CELLS

| SUBJECT POPULATION | SUBJECTS WITH DETECTABLE SURFACE $Ig^+$ T CELLS[1] |
|---|---|
| HIV-1 SEROPOSITIVE | 33/52 (63%) |
| Asymptomatic (CDC stages II and III) | 19/27 (70%) |
| Symptomatic (CDC stage IV) | 14/25 (56%) |
| HIV-1 SERONEGATIVE | 0/44 (0%) |
| Homosexual/Bisexual | 0/30 (0%) |
| Heterosexual | 0/14 (0%) |

[1]Subjects with ≧2% surface $Ig^+/CD3^+$ lymphocytes in their blood.

In the $Ig^+$ subjects, from 2–88% of the $CD3+$ cells were surface $Ig^+$ (median 18%; mean 26%). The majority of asymptomatic (Storage II and III by CDC classification, Center for Disease Control, U.S. Department of Health and Human Services, Classification system for human T-lymphotropic virus type III/lymphadenopathy-associated virus infections (1986) Ann. Int. Med. 105:234–237 (CDC classification)), and symptomatic (Stage IV by the CEC classification) subjects contained surface $Ig^+$ T cells in their blood. In the asymptomatic group, only one subject had a history of intravenous drug abuse (IVDA) and only two subjects had received blood transfusions previously. In the symptomatic group, nine subjects had a history of IVDA (five of whom had surface Ig+ T cells) and four subjects had received blood transfusions (two of whom had surface IG+ T cells). These data indicate that a history of neither IVDA nor blood transfusion is related to the presence of surface Ig+ T cells. The presence of surface Ig T cells was specific for HIV infection in that no seronegative individuals (n=44) contained such cells in their blood.

Isotype determination of the surface Ig on T cells revealed both IgG and IgM antibodies in 9 of 10 Ig subjects tested. One subject had only IgM antibody detectable on his T cells.

Figure 1:
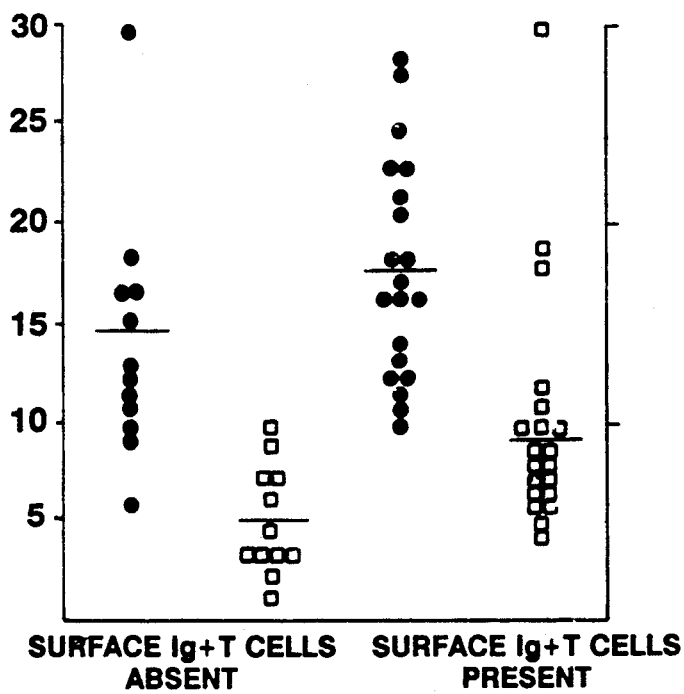
FIG. 1 is a graph illustrating the relationship between the presence of surface $Ig^+$ cells and the plasma-IgG and plasma-IgM concentration.
Figure 2:
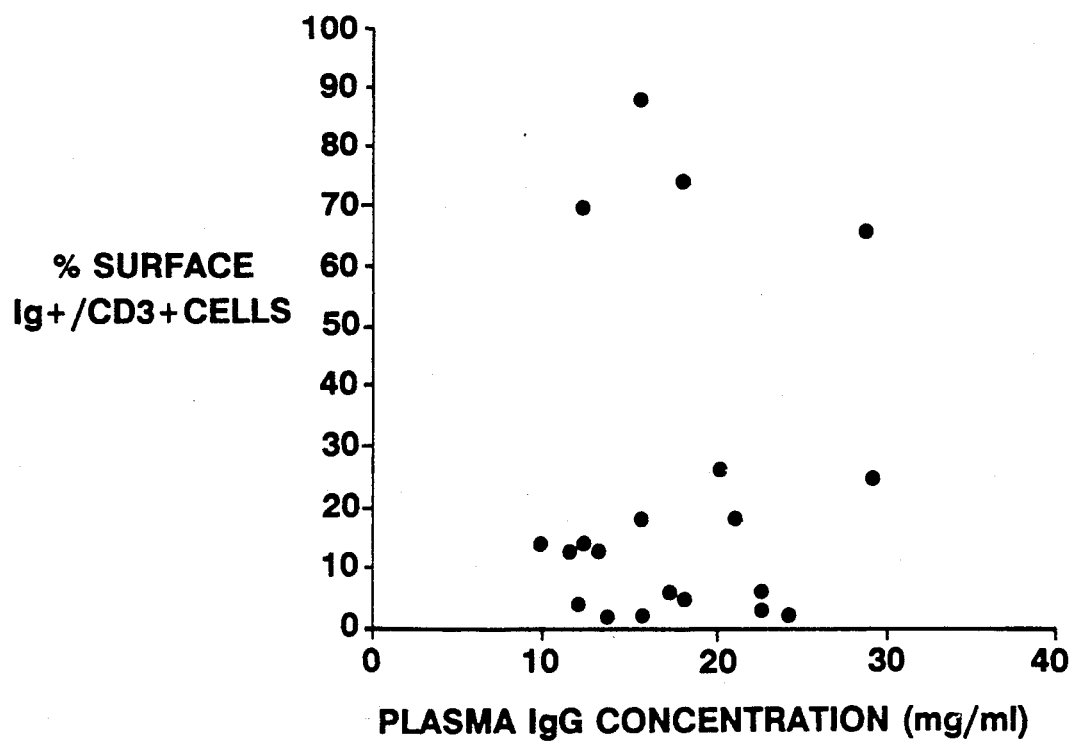
FIG. 2 is a graph of the percentage of surface $Ig^+/CD3^{30}$ cells in $Ig^+$ subjects as a function of plasma IgG concentration.

To determine if the presence and/or number of surface Ig+ T cells was dependent upon plasma immunoglobulin levels, plasma was analyzed by ELISA for IgG and IgM concentrations, as described below. FIG. 1 shows a comparison of plasma IgG (filled circles) and IgM (open squares) concentrations in individuals with and within surface Ig+ T lymphocytes. Each filled circle or open square represents one HIV-1 seropositive subject. The horizontal bars represent the mean plasma Ig concentrations for each group of individuals. Although subjects with surface Ig+ T cells tended to have higher plasma immunoglobulin concentrations, the level of plasma IgG or IgM could not be used to identify individuals with surface Ig+ T cells because of a substantial overlap in the Ig concentration values between these groups. Moreover, in subjects who had surface Ig+ T cells, there was no correlation between the percentage of positive cells and the plasma IgG concentration. The percentage of surface Ig+/CD3+ cells as a function of the plasma IgG concentration in 20 subjects is shown in FIG. 2. There is no correlation between the percentage of surface Ig+/CD3+ cells and the plasma IgG concentration (r=0.009). Taken together, these data suggest that non-specific adherence of Ig to T cells cannot explain the presence of surface Ig+ T cells in HIV-1 seropositive individuals.

It was also considered that surface Ig+ T cells could result from anti-HIV-1 antibodies that were bound to T cells via a viral antigen intermediate. However, in the 33 subjects found to have surface Ig+ T cells, the median percentage of surface Ig+ T cells was 18%. In contrast, a very small percentage (<0.01%) of blood mononuclear cells from seropositive individuals have been found to express HIV-1 RNA, Harper et al. (1986) Proc. Natl. Acad. Sci. USA 83:772–776. Moreover, immunofluorescent staining of T lymphocytes from HIV-1 infected subjects using anti-HIV-1 serum (containing no anti-T cell antibodies) never detects positive cells. Thus, the surface Ig+ T cells noted in the present study are not likely a result of antiviral antibody binding to lymphocytes that are HIV-1 infected or display absorbed viral proteins.

Surface Ig+ T lymphocytes were detected as follows. Blood was obtained from HIV-1 seropositive individuals at the New England Medical Center Hospital, the Boston City Hospital and the Fenway Community Health Center in Boston, Mass. Blood from HIV-1 seronegative homosexual and bisexual men was obtained through the Fenway Community Health Center and blood from HIV-1 seronegative, heterosexual individuals was obtained from laboratory personnel at the New England Medical Center Hospital. Data from all blood specimens obtained were included herein. The clinical status of HIV-infected individuals was determined by their physician in accordance with staging criteria from the CDC classification. The complete blood counts and lymphocyte subset phenotype data were obtained from the institution at which the blood specimens were obtained.

Peripheral blood mononuclear cells were isolated from freshly obtained, heparanized blood by Ficoll-Hypague (Pharmacia Fine Chemicals, Piscataway, N.J.) density centrifugation. The cells were washed three times in phosphate-buffered saline (PBS) containing 1% bovine serum albumin (BSA) and 0.2% sodium azide and then subjected to a two step staining procedure using this buffer. The cells were first reacted for 30 minutes at 4° C. with a 1:10 dilution of biotinylated goat anti-human Ig F(ab')$_2$ (Tago Inc., Burlingame, Calif.) that had been previously absorbed extensively on mouse immunoglobulins coupled to Sepharose-4B (Pharmacia). After washing, the cells were then reacted with a mixture of fluorescein isothiocyanate conjugated (FITC) Streptavidin (Zymed Laboratories, Inc., So. San Francisco, Calif.) (1:50 dilution) and a phycoerythrin-conjugated monoclonal antibody to either CD3, CD4, or CD8 (OKT3, OKT4, OKT8; Ortho Diagnostic Systems Inc., Raritan, N.J.) (1:10 dilution). After a further incubation of 30 minutes, the cells were washed, fixed in 1% formalin and analyzed on an EPICS V flow cytometer with a multiparameter data aquisition and display system (Coulter Corporation, Hialeah, Fla.). Fluorescence was measured on the cell population which contained the majority (>90%) of the CD3+ lymphocytes. Samples were scored positive for surface Ig+ T cells if 2% or more cells stained with both the anti-T cell and anti-human Ig reagents. This value was chosen as the test cutoff based on results of HIV-1 seronegative, heterosexual volunteers (n=14) in which surface Ig+ T cells averaged 1.0±0.8% (3 standard deviations of the mean).

Plasma immunoglobulin concentration was determined as follows. Immulon II 96 well polystyrene plates (Dynatech Laboratories, Inc., Alexandria, Va.) were coated with goat anti-human Ig (5 μg/ml) (Tago Inc.) diluted in PBS, pH 7.2, overnight at 37° C. The wells were blocked with 5% BSA in PBS for one hour at room temperature followed by the additon of duplicate samples of heat-inactivated human plasma diluted 1:150,000 (for IgG assays) or 1:15,000 (for IgM assays) in 1% BSA in PBS for one hour at room temperature. Fivefold serial dilutions of affinity purified human IgG or IgM (1 mg/ml) (Jackson Immunoresearch Laboratories Inc., West Grove, Pa.) were also added to wells on each polystyrene plate for generation of standard concentration curves. The wells were washed five times with PBS containing 0.1% Tween 20 (Fisher Scientific Co. Fair Lawn, N.J.) followed by the addition of biotinylated F(ab')$_2$ fragments of goat anti-human IgG or anti-human IgM (Tago Inc.) diluted 1:1500 in 1% BSA in PBS. After a one hour incubation at room temperature, the wells were washed and alkaline phosphatase-conjugated avidin (Boeheringer Mannheim Biochemicals, Indianapolis, Ind.) diluted 1:800 in 1% BSA/PBS was added for one hour at room temperature. The wells were washed and then developed using phosphatase substrate (1 mg/ml) (Sigma Chemical Company, St. Louis, Mo.) dissolved in 0.05 M sodium bicarbonate, 0.002 M magnesium chloride, pH 9.5. Absorbance ($A_{405}$) was measured on an automated ELISA spectrophotometer (Dynatech Laboratories, Inc.)

Figure 3:
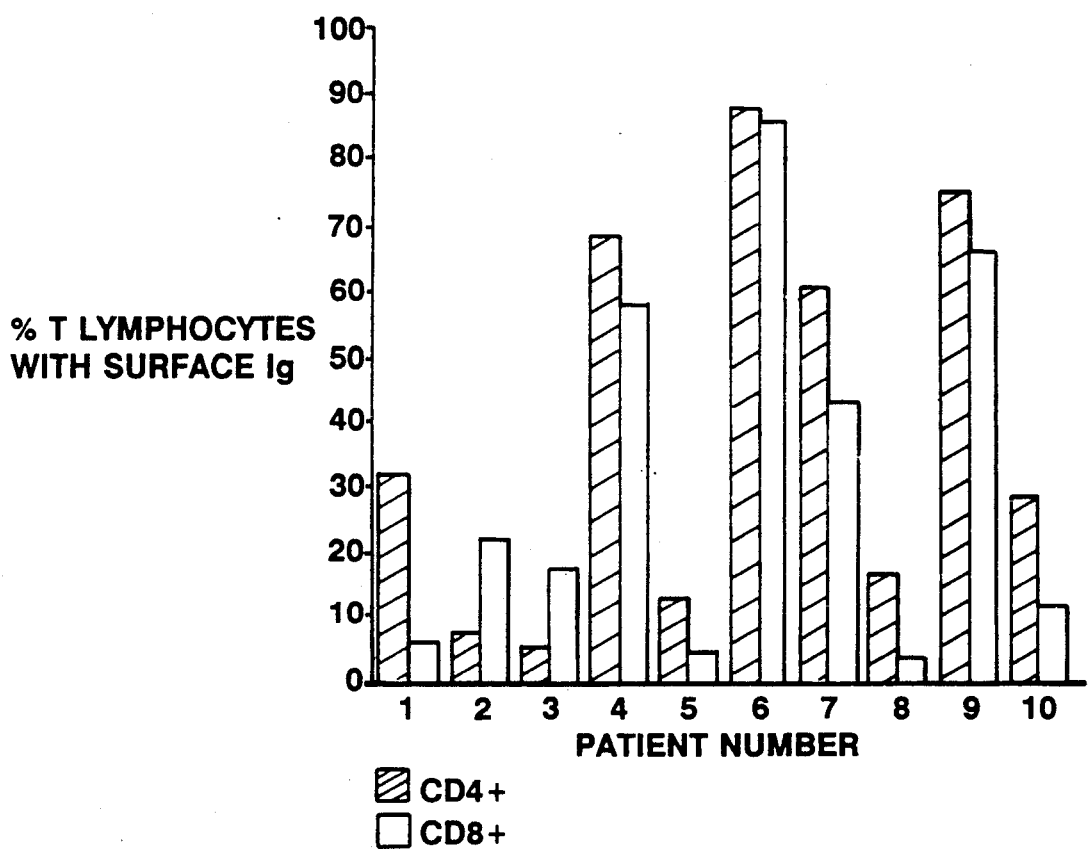
FIG. 3 is a graph illustrating the distribution of surface $Ig^+$ cells between the $CD4+$ and $CD8+$ subsets.

Surface Ig+ T Cells are Correlated With Low CD4+ Counts in Asymptomatic Individuals To investigate the distribution of the surface Ig+/CD3+ cells between the CD4+ and CD8+ T cell subsets, peripheral blood mononuclear cells from ten Ig+ subjects were tested, as described below, for the presence of surface Ig+ /CD4+ and surface Ig+/CDC8+ cells. All ten subjects were found to have surface Ig on both CD4+ and CD8+ cells, FIG. 3. In five of these individuals, immunoglobulin was detected on greater than 20% of the cells in each T cell subset.

To determine if the presence of surface Ig+ T lymphocytes correlated with low lymphocyte counts, the absolute T cell subset counts were analyzed in subjects stratified according to the presence of clinical symptoms (i.e., asymptomatic vs. symptomatic). In asymptomatic subjects, the presence of surface Ig+ T cells correlated strongly with lower CD4+ cell counts ($p<0.001$), whereas in symptomatic subjects, no correlation was noted between the presence of surface Ig+ T cells and the absolute CD4+ cell counts, Table 2. The CD8+ cell counts did not differ significantly between any group.

TABLE 2

RELATIONSHIP OF SURFACE Ig+ T CELLS TO ABSOLUTE T CELL SUBSET COUNTS IN HIV-1 SEROPOSITIVE SUBJECTS

| | Asymptomatic Subjects | | Symptomatic Subjects | |
|---|---|---|---|---|
| | Without Surface Ig+ T cells (n = 8) | With Surface Ig+ T cells (n = 19) | Without Surface Ig+ T cells (n = 11) | With Surface Ig+ T cells (n = 14) |
| CD3+ cells | 2228 ± 670[1] | 1432 ± 630 | 894 ± 424 | 1094 ± 606 |
| CD4+ cells | 1104 ± 295 | 466 ± 279[2] | 272 ± 267 | 243 ± 164 |
| CD8+ cells | 987 ± 375 | 887 ± 445 | 625 ± 303 | 743 ± 385 |

[1] values represent mean cell count ± 1 standard deviation
[2] $p < .001$

Surface Ig+ T Cells are Correlated with the Presence of Anti-T Cell Antibodies To assess the potential contribution of anti-T cell antibodies to the generation of surface Ig+ T cells, we determined whether subjects with surface Ig+ T cells had serum antibodies that could bind to normal T cells. For this purpose, sera were tested for binding to concanalavin A/interleukin 2-stimulated peripheral blood T lymphocytes from normal donors, as described below. Serum anti-T cell antibodies were detected in over 80% of subjects with surface Ig+ T cells but in only 18% of subjects without surface Ig+ T cells, FIG. 3. The presence of anti-T cell antibodies appeared specific for HIV-1 infection in that none of 18 HIV-1 seronegative individuals with chronic hepatitis B antigenemia (HBsAg) had such antibodies in their sera.

Figure 4:
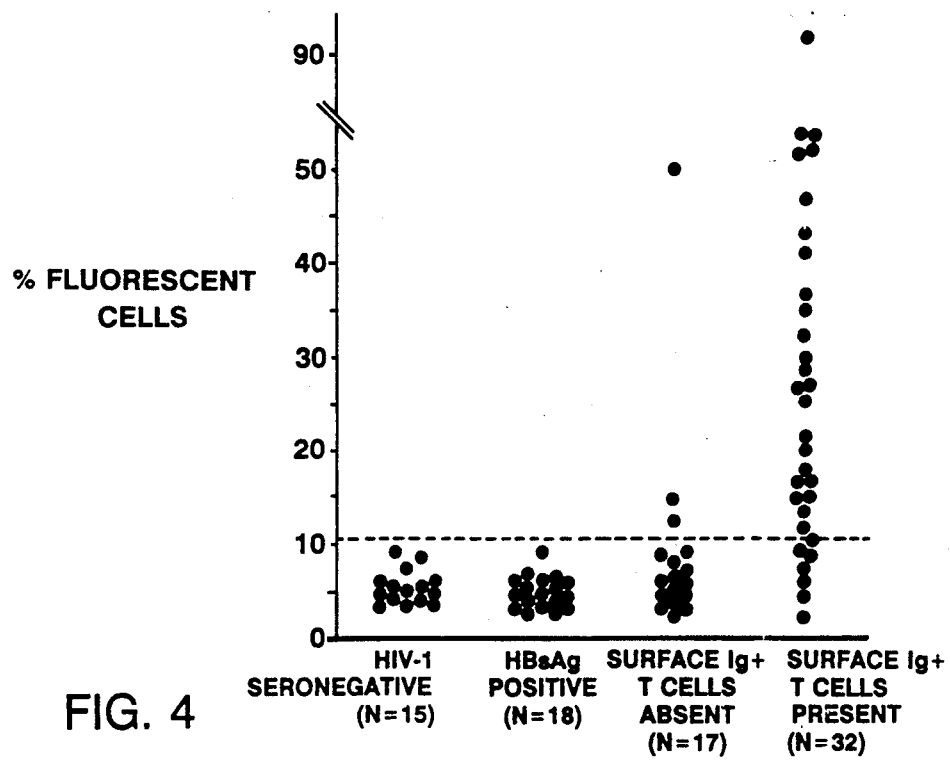
FIG. 4 is a graph illustrating the relationship between the presence of anti-T lymphocyte antibodies and surface $Ig^+$ lymphocytes.

FIG. 4 shows the relationship of anti-T lymphocyte antibodies to surface Ig+ T lymphocytes. Peripheral blood mononuclear cells from normal donors were activated for three days with concanavalin A (5 μg/ml) and grown for 5 subsequent days in the presence of recombinant interleukin-2 (50 units/ml). Heat inactivated sera (1:50 dilution) from four different subject groups were tested for binding by indirect immunofluorecence to the activated T cells. Percent fluorescent cells were determined with respect to a buffer control. The dotted line represents 3 standard deviations above the mean fluorescence obtained using sera from 15 healthy, HIV-1 seronegative donors. The results shown are representative of those obtained using T cell lines from three unrelated normal donors Serum anti-T lymphocyte antibodies were detected as follows. Sera were heat inactivated, diluted 1:50 in staining buffer and tested for binding to T cell lines obtained from HIV-1 seronegative donors. After a 30 minute incubation with sera at 4° C., the cells were washed and binding of antibody was detected by the staining procedure described above. Percent fluorescent cells were determined by flow cytometry. Background (0%) fluorescence was obtained by substituting staining buffer for sera in the first step of the incubation.

Autoantibodies in Sera From HIV-1 Infected Subjects Bind CD43

Figure 5:
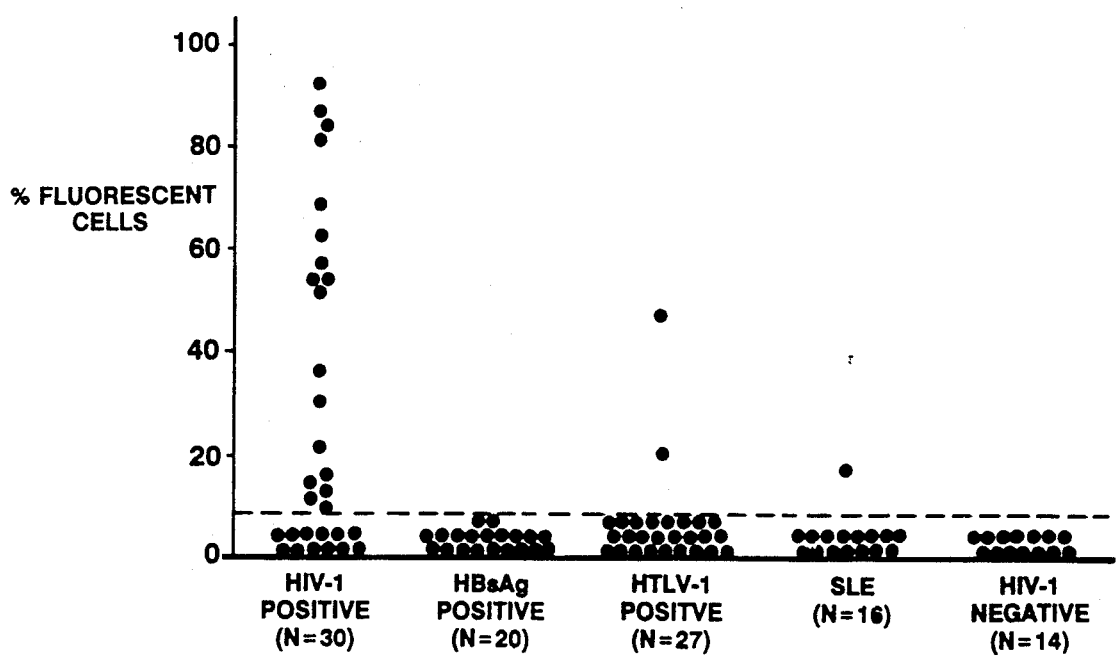
FIG. 5 is a graph illustrating the distribution of serum antibodies capable of binding to SupT cells.

To determine if antibodies to native T cell surface antigens could be detected in the sera of seropositive subjects, sera from HIV-1 infected subjects were screened by immunofluorsecent flow cytometry to identify those containing antibodies that could bind to a CD4+/CD8+ positive, T cell (thymic) leukemia line termed SupT1 (AIDS Research and Reference Reagent Program Catalog, NIH Publication No. 90-1536, Division of AIDS, National Institute of Allergy and Infectious Diseases, 6003 Executive Boulevard, Bethesda, Md. 20892; Smith et al. (1984) Cancer Res. 44:5657). This cell line expresses high levels of native CD4 and is susceptible to HIV-1 infection in vitro, Hoxie et al. (1986) Science 234:1123-1127. Serum from several HIV-1 seropositive individuals contained antibodies which stained the SupT1 leukemia cell line, FIG. 5. In FIG. 5 percent fluorescent cells indicates the percentage of cells stained by each serum after subtraction of the percentage of cells stained by control, pooled normal human sera (previously determined to contain no antibodies that could immunoprecipitate any SupT1 surface protein). Each dot represents the percentage of cells stained by an individual serum. The horizontal dotted line indicates 3 standard deviations above the mean percentage of cells stained by sera from 14 healthy, individually tested, HIV-1 seronegative laboratory personnel. In contrast, no sera from hepatitis B-antigenemic individuals (HBsAg+) and few sera from individuals seropositive for HTLV-1 infection or with the autoimmune disease systemic lupus erythematosus (SLE) demonstrated staining of SupT1 cells greater than sera from healthy, HIV-1 seronegative control subjects.

Figure 6:
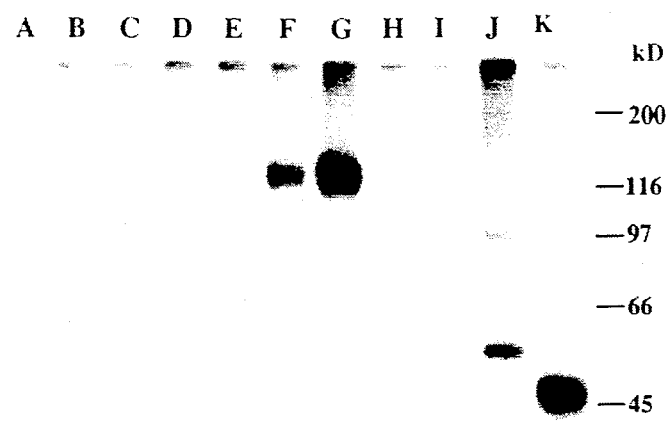
FIG. 6 is a photograph of a gel loaded with SupT1 surface proteins immunoprecipitated by lymphocyte eluates

To identify the T cell surface molecule(s) bound by the serum antibodies, sera were absorbed to SupT1 cells and the eluted antibodies (eluates) were used to immunoprecipitate detergent-solubilized lysates from $^{125}$I-labelled SupT1 cells, all as described below. Of eighteen eluates prepared from different HIV-1 positive sera (sera also positive for SupT1 staining), none immunoprecipitated CD4. However, eight separate eluates immunoprecipitated a single SupT1 surface protein with a relative molecular mass ($M_r$) of 120 kilodaltons (kD) as determined by SDS-polyacrylamide gel electrophoresis (SDS-PAGE). FIG. 6 shows representative analysis of the SupT1 surface protein immunoprecipitate by the human antibody-containing eluates. Antibodies: normal human IgG, 1 ug (lane A); eluates from two different HIV-1 negative sera, 0.25 ug IgG (lanes B and C); eluates from two different HIV-1 positive sera that did not stain SupT1 cells, 0.25 ug IgG (lanes D and E); eluates from four different HIV-1 sera that did stain SupT1 cells, 0.25 ug IgG (lanes F through I); anti-leu 3a (Becton-Dickinson), an anti-CD4 monoclonal antibody, 1 ug (lane J); OKT6 (Ortho Diagnostics), an anti-CD1 monoclonal antibody, 1 ug (lane K). The 120 kD protein was not immunoprecipitated by eluates prepared from the two HTLV-1 positive sera and the one SLE serum that did stain the SupT1 cells. Antibodies that immunoprecipitated the 120 kD SupT1 protein could be detected only in HIV-1 positive sera. Of the eight patients with such antibodies, all had low absolute CD4+ lymphocyte counts (<400 CD4+cells/$\mu$l blood), and six had histories of opportunistic infections.

Figure 7:
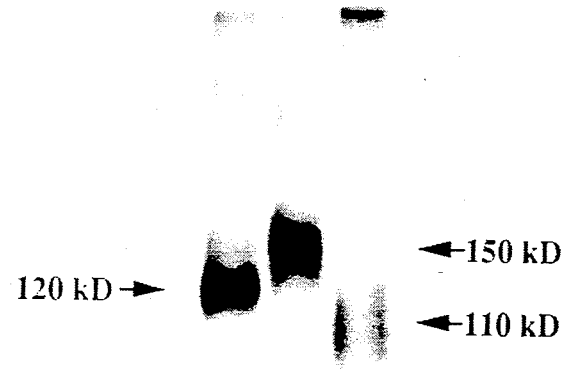
FIG. 7 is a photograph of a gel showing the biochemical characterization of the 120 kD SupT1 protein.

Neuraminidase digestion, performed as described below, of the immunoprecipitated 120 kD SupT1 protein shifted its $M_r$, as determined by SDS PAGE, to approximately 150 kD. This result is consistent with removal of negatively charged sialic acid residues, Carlsson et al. (1986) J. Biol. Chem. 261:11279–12786, Borche et al. (1987) Eur. J. Immunol. 17:1523–1526. Subsequent O-Glycannase digestion of the neuraminidase treated immunoprecipitate resulted in a $M_r$ of approximately 110 kD as determined by SDS-PAGE, indicating the presence of O-glycosidic linkages. FIG. 7 shows the biochemical characterization of the 120 kD SupT1 protein. Three equal aliquots of lysates from radiolabelled SupT1 cells were immunoprecipitated by 0.25 ug of pooled eluate IgG (previously demonstrated to contain antibodies to the 120 kD SupT1 protein) and were left undigested (−), digested with neuraminidase (N), or digested with neuraminidase followed by O-Glycanase (N/O) and analysed by SDS-PAGE. These biochemical characteristics suggested that the 120 kD SupT1 protein was similar to CD43, a cell surface sialoglycoprotein predominantly expressed by cells of hematopoetic origin, Brown et al. (1981) Nature 289:456, Carlsson et al. (1986) J. Biol. Chem. 261:11274–12786, Killeen et al. (1987) EMBO J. 6:4029–4034, Borche et al. (1987) Eur. J. Immunol. 17:1523–1526, Mentzen et al. (1987) J. Exp. Med. 165:1383–1392, and Carlsson et al. (1986) J. Biol. Chem. 261:12787–12795.

Figure 8:
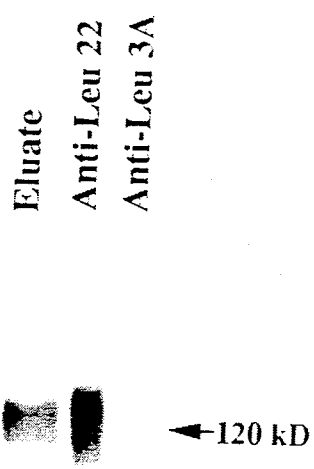
FIG. 8 is a photograph of an immunoblot of the 120 kD SupT1 protein.
Figure 9:
FIG. 9 is a gel showing the immunoprecipitation of CD43 from COS cells.

The results of two experiments established that the 120 kD protein immunoprecipitated by the eluates is CD43. First, a monoclonal anti-CD43 antibody (anti-leu 22; clone L60 [Fourth International Workshop on Leukocyte Differentiation Antigens, 1989]) bound to the 120 kD SupT1 protein that was immunoprecipitated by pooled eluates and then electroblotted onto nitrocellulose paper. FIG. 8 provides immunoblot evidence that the 120 kD SupT1 protein is CD43. Equal aliquots of a lysate prepared from $60 \times 10^6$ unlabelled SupT1 cells were immunoprecipitated by 0.25 ug of pooled eluate IgG (Eluate); by 0.5 ug of anti-leu 22 (Becton Dickinson), an anti-CD43 monoclonal antibody (Anti-Leu 22); or by 0.5 ug of anti-Leu 3a, an anti-CD4 monoclonal antibody used as a control (Anti Leu 3A). The immunoprecipitates were resolved by SDS-PAGE under reducing conditions, electroblotted onto 0.45 micron nitrocellulose paper (Towbin et al. (1979) Proc. Natl. Acad. Sci. USA 76:4350), and probed with anti leu 22. Second, the eluates immunoprecipitated a 130 kD protein from COS cells (SV 40 transformed African Green monkey kidney cells (ATCC CRL 1650; ATCC CRL 1651); Seed et al. (1987) Proc. Natl. Acad. Sci. U.S.A. 84:3365-3369) transfected with a cDNA clone encoding CD43 but not from control COS cells transfected with a cDNA clone of ICAM-1. Anti-leu 22 specifically immunoprecipitated a protein with a $M_r$ of 120 kD from the CD43-transfected COS cells, suggesting that anti leu 22 recognizes a form of CD43 that is more sialylated than the CD43 form recognized by the eluates, Carlsson et al. (1986) J. Biol. Chem. 261:11279–12786, and Borche et al. (1987) Eur. J. Immunol. 17:1523–1526. FIG. 9 demonstrates the immunoprecipitation of CD43 from COS cells transfected with a cDNA clone encoding CD43. Separate sets of COS cells were transiently transfected using DEAE-dextran with the CD43 cDNA clone PEER-3 (Pallant et al. (1989) Proc. Natl. Acad. Sci, USA 86:1328) inserted into the CDM8 plasmid vector (Seed et. al. (1987) Proc. Natl. Acad. Sci. USA 84:3365.), or with a control cDNA encoding ICAM 1 (Staunton et. al. (1989) Nature 339:61), also inserted into the CDM8 plasmid. Three days later, each set of transfected cells were surface iodonated and cell lysates were immunoprecipitated by 0.25 ug pooled eluate IgG (lane A) or by 0.5 ug of anti-leu 22 (lane C). Control lysates from the radiolabelled ICAM-1 transfectants were immunoprecipitated by 0.25 ug of pooled eluate (lane B), by 0.5 ug of anti-leu 22 (lane D) or by 0.5 ug of RR1/1, an anti-ICAM-1 monoclonal antibody (Staunton (1989) Nature 339:61) (lane E).

Immunofluorescent screening of sera for antibodies that could bind to the SupT1 leukemia cell line was performed as follows. Sera clarified by centrifugation (10,000 g $\times$ 10 min.) were diluted 1:50 in phosphate-buffered saline containing 1% bovine serum albumin and 0.2% sodium azide (staining buffer) and incubated for 30 minutes on ice with SupT1 cells. After washing in staining buffer, the cells were incubated for 30 minutes on ice with fluorescein isocyanate conjugated oat anti human IgG F(ab')$_2$ (Tago, Inc., Burlingame, Calif.) diluted 1:60 in staining buffer. The cells were then washed, fixed in 1% formalin and analyzed on a EPICS 541 flow cytometer (Coulter).

The eluates were prepared by incubating 1 ml of human serum (diluted 1:40 in PBS, pH 7.2 containing 1% BSA and 0.2% sodium azide) with $10^9$ SupT1 cells for 2 hours at 4° C. The cells were washed 4 times with 50 ml of ice-cold PBS and the bound antibodies were eluted using 2 ml of 0.1 M glycine, pH 2.5 for 2 minutes on ice. The cells were removed by centrifugation (1000$\times$g). The eluates were neutralized with 200 ul of 1M Tris pH 8.0 and then dialysed extensively against PBS, pH 7.2 prior to use. Antibody concentration of the eluates was determined by ELISA.

Immunoprecipitation experiments of radiolabelled cells were performed as follows. $20 \times 10^6$ SupT1 cells (or $5 \times 10^6$ transfected COS cells (COS cells were transfected as described in Seed et al. (1987) Proc. Acad. Sci. USA 84:3365-3369)) were surface labelled with 1 $\mu$Ci of $^{125}$I (Amersham) using lactoperoxidase and then solubilized in lysis buffer (Tris-buffered saline containing 1% Triton-X-100 and 1 mM phenlymethysulfonylfluoride (PMSF)). The cell lysates were clarified by centrifugation and precleared with Protein A-Sepharose Beads (Pharmacia). Antibodies were prebound to Protein A-Sepharose beads and the antibody-bead complexes were incubated overnight at 4° C. with equal aliquots of radiolabelled cell lysate. The beads were washed 6 times in lysis buffer, the immunoprecipitates were eluted from the beads by heating in sample buffer (containing 0.45% SDS, 2% glycerol and 0.1% 2-mercaptoethanol), and the samples were resolved by SDS-PAGE (10% acrylamide). The immunoprecipitated proteins were detected by autoradiography of the dried gel using an intensifying screen at −70° C. Exposure time was four days for all autoradiographs.

For the enzyme digestion experiments, immunoprecipitation digestions were performed as follows: neuraminidase (Calbiochem), 0.1 u/ml for 60 minutes at 37° C, O-Glycanase (Genzyme), 4 milliunits/ml ×18 hr at 37° C. The enzyme reaction mixtures contained 0.17% SDS, 0.3% 2-meracaptoethanol, 1.25% Nonidet-40 (NP-40), 5 mM calcium carbonate, 10 mM phenanthroline and 20 mM sodium cacodylate, pH 6.5. The non-digested and digested immunoprecipitates were resolved by SDS-PAGE and autoradiographed, as described above. For the immunoblotting experiment, the nitrocellulose paper (Schleicher and Scheull) was blocked in 0.05 M Tris buffered saline, pH 7.0 containing 5% non fat dry milk (blocking buffer) and then reacted with anti-leu 22, 1 µg/ml diluted in blocking buffer for 18 hours at 4° C. The blot was washed extensively in blocking buffer and then reacted with alkaline phosphatase-conjugated goat anti-mouse Ig (Boehringer Mannheim) diluted 1:600 in blocking buffer for 2 hours at room temperature. After further extensive washing, the blot was developed with a precipitating substrate, Blake et al. (1984) Anal. Biochem 136:175–179.

Serum Autoantibodies from HIV-1 Infected Individuals Bind CD43 found on Thymocytes To determine if the eluates could bind to normal human cells of thymic lineage (from seronegative subjects) known to express CD43, two eluates (from two different HIV-1 infected subjects) containing anti-CD43 antibodies were tested for binding to thymocytes, fresh peripheral blood T lymphocytes and phytohemagglutinin-activitated T lymphocytes that had been maintained in interlukin 2, as described below. The eluates bound only to thymocytes, whereas the anti-CD43 monoclonal antibody (anti-leu 22) bound to all three cell types. However, the eluates bound to all cell types if the cells were first treated with neuraminidase, a treatment that eliminated the epitope recognized by anti-leu 22.

Figure 10:
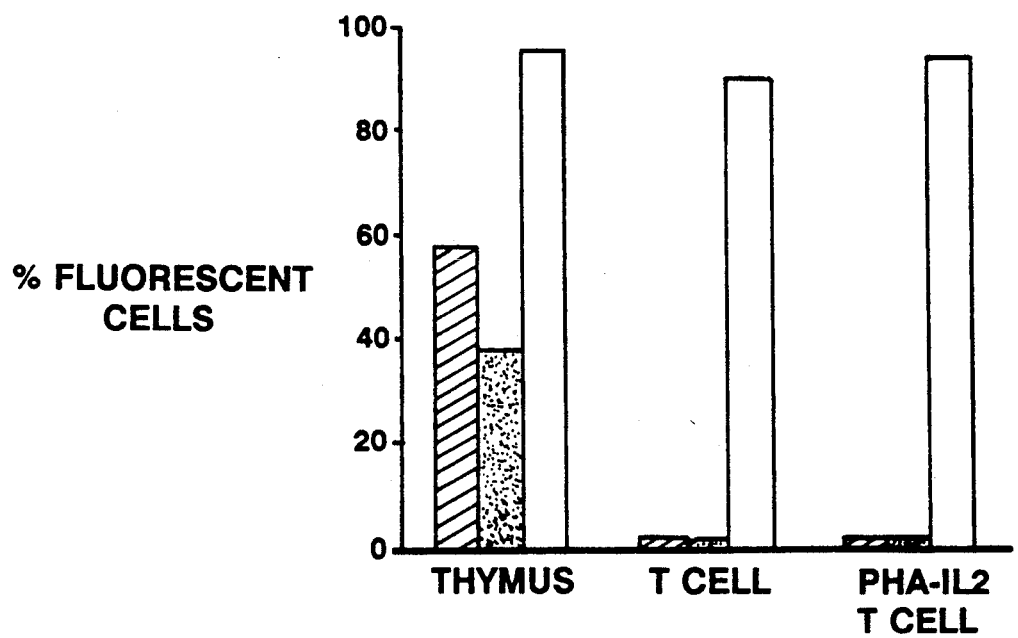
FIG. 10 is a graph illustrating the ability of T cell eluates and anti-leu 22 to bind thymocytes, T lymphocytes, and activated T lymphocytes.
Figure 11:
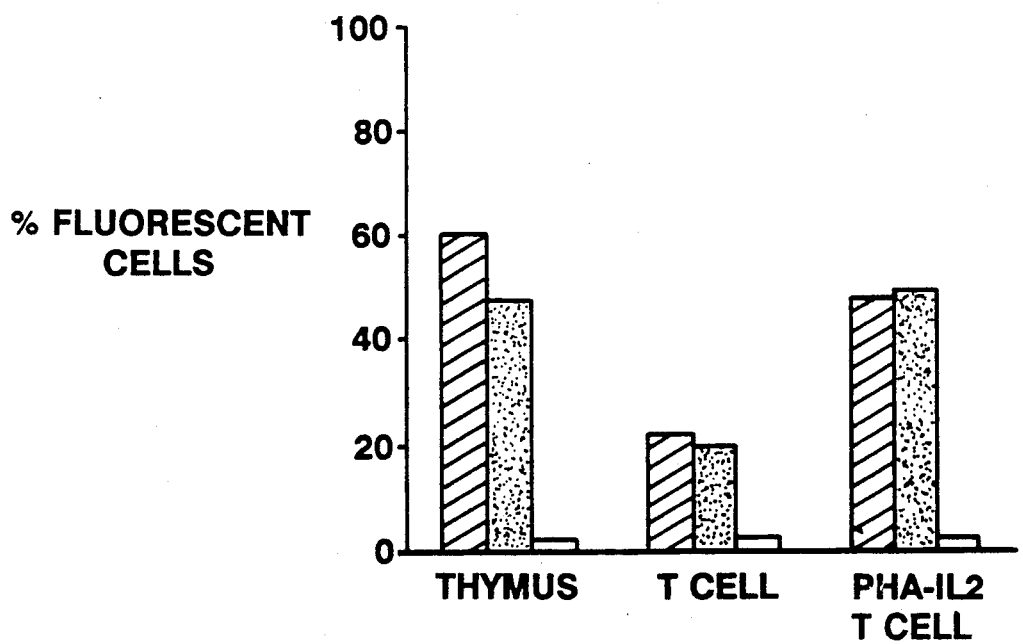
FIG. 11 is a graph illustrating the ability of T cell eluates and anti-leu 22 to bind neuraminidase-treated thymocytes, T lymphocytes, and activated T lymphocytes.

FIG. 10 shows that eluates bind to normal thymocytes but not to normal T lymphocytes. FIG. 11 shows that eluates bind to all three cell types after cells have been treated with neuraminidase (0.1 U/ml in RPMI 1640 (Irvine Scientific) for 30 minutes at 37° C.), but that the reactivity of anti-leu 22 is lost. In both FIG. 10 and FIG. 11 eluates from patients M-1 (grey bars) and E-1 (black bars), and anti-leu 22 (white bars) were tested by indirect immunofluorescence for binding to thymocytes (THYMUS), peripheral blood T lymphocytes (T CELLS), and T lymphocytes stimulated with phytohemagglutinin for 3 days and maintained in interlukin 2 for seven days (PHA-IL2 T CELLS). The results are representative of 3 separate experiments in which thymocytes and T lymphocytes from other donors were tested.

These results suggested that the eluates recognize a non-sialic acid epitope of CD43 present on both thymocytes and mature T lymphocytes, but accessible to antibody binding only on thymocytes.

Figure 12:
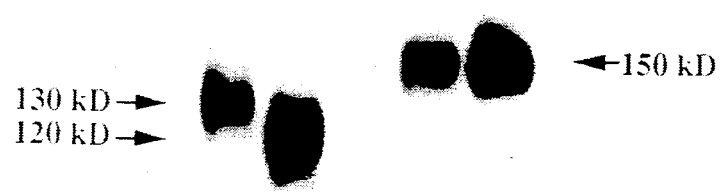
FIG. 12 is a photograph of a gel that shows the immunoprecipitation of CD43 from thymocytes by eluates.

Immunoprecipitation of cell lysates from radiolabelled thymocytes confirmed that the eluates contain autoantibodies that recognize a partially sialylated form of CD43. The pooled eluates immunoprecipitated a single protein with a $M_r$ of approximately 130 kD whereas anti-leu 22 immunoprecipitated a protein with a $M_r$ of approximately 120 kD. However, after digestion of each immunoprecipitate with neuraminidase, the proteins immunoprecipitated by the pooled eluates and anti-leu 22 migrated identically with a $M_r$ of 150 kD. FIG. 12 shows the immunoprecipitation of CD43 from normal human thymocytes by the pooled eluates (lanes A and C) and anti-leu 22 (lanes B and D). The immunoprecipitates in lanes C and D were treated with neuraminidase (0.1 U/ml) prior to electrophoresis. 0.5 ug of pooled eluates or 0.5 ug of anti-leu 22 were used to immunoprecipitate equal aliquots of $^{125}$Iodine-labelled cell lysate from $40 \times 10^6$ normal thymocytes. SDS-PAGE and autoradiography was performed as described above. These results are consistent with those from the COS cell transfection experiments where two forms of CD43 were identified. Taken together with the immunofluorescent results, the data confirm that a partially sialylated CD43 is normally expressed on a large subpopulation of thymocytes but not on mature T lymphocytes.

Determination of the ability of eluates to bind normal cells of thymic lineage was performed as follows. In the immunofluorescence experiments two different eluates (each containing approx. 0.5 µg/ml IgG) and anti-leu 22 (1 µg/ml) were used. Phytohemagglutinin (Sigma) was used at 5 µg/ml and interleukin 2 (Cetus) at 100 units/ml. The thymocytes were obtained from a 22 month old infant undergoing open heart surgery for congenital heart disease. The T lymphocytes were obtained from a healthy, HIV-1 negative adult donor. Neuraminidase treatment of cells was performed in RPMI 1640 (Irvine Scientific) with 0.1 units/ml of neuraminidase (Calbiochem) at 37° C. for 30 min. Binding of eluates to peripheral blood T lymphocytes was analysed using two colors of fluorescence in which the T cells were identified by phycoerythrin-conjugated OKT3 (Ortho Diagnostics), a monoclonal anti-CD43 antibody that stains 60–80% of peripheral blood lymphocytes. The results were representative of two separate experiments in which thymocytes and T lymphocytes from other donors were tested. For the immunoprecipitation experiment, 0.5 µg of anti-leu 22 were used to immunoprecipitate equal aliquots of $^{125}$iodine-labelled cell lysate from $40 \times 10^6$ normal thymocytes. SDS-PAGE and autoradiography was performed as described above.

Production of a soluble CD43 fragment

As described above, individuals infected with HIV-1, but not uninfected individuals, possess autoantibodies to the CD43. The anti-CD43 autoantibodies bind to immature T-lymphocytes, and possibly to other cells, e.g., brain cells which carry anti-CD43 autoantibody binding sites on their surfaces. In the case of lymphocytes, the binding of anti-CD43 autoantibodies mark them for destruction or cause them to function abnormally, thus contributing to immune delivery.

The soluble CD43 fragments of the invention have the capacity to prevent the binding of anti-CD43 autoantibodies to antigens present on cell surfaces by competing with these antigens for available anti-CD43 autoantibodies. Thus the administration of soluble CD43 fragments can prevent the unwanted and deleterious binding of anti-CD43 autoantibodies to cells. Fragments of CD43 are also useful in diagnosing presence of anti-CD43 autoantbodies. Methods well known to those skilled in the art allow for the production of useful quantities of soluble CD43 fragments.

The gene encoding CD43 has been cloned and the DNA sequence of the gene and the amino acid sequence of the protein have been published, Pallant et al. (1989) Proc. Natl. Acad. Sci. USA 86:1328–1332, hereby incorporated by reference, and Shelley et al. (1989) Proc. Natl. Acad. Sci. USA 86:2819–2823, hereby incorporated by reference. FIG. 13 shows the nucleotide and deduced amino acid seuqence of sialophorin cDNA. The depicted sequence is that of the HPB1.9 insert (Shelley et al. (1989) Proc. Natl. Acad. Sci. USA 86:2819-2823). Amino acids are numbered on the left and nucleotides on the right. The transmembrane domain is boxed and emboldened. Asn-239 is the single N-linked glycosylation site. The only discrepancy is residue 360, identified as lysine by amino acid sequencing and glutamic acid in the deduced sequence. The protein sequence includes, in the following order, an amino acid leader peptide approximately 19 residues in length (amino acid residues 1-approximately 19 in FIG. 13), a 235-amino acid residue extracellular domain (amino acid residues 20–254 in FIG. 13), a 23 amino acid residue transmembrane domain (amino acid residues 255–277 in FIG. 13), and a 123-amino acid residue intracytoplasmic domain (amino acid residues 278–400 in FIG. 13). A soluble CD43 fragment can be produced by (1) genetic engineering of the CD43 sequence to delete the leader sequence, the sequence encoding the transmembrane region (or those sequences which encode the portions of the transmembrane region which result in insolubility), and the intracellular sequence, (2) inserting the sequence encoding the desired portion of CD43 in an expression vector, and (3) expressing the soluble CD43 fragment in an expression system. The methods of DNA manipulation, the expression vectors, and the expression systems referred to are well known to those skilled in the art. A preferred soluble CD43 fragment includes all or most of the extracellular region of the protein, i.e., all or most of the amino acid residues between positions 20 and 254 in FIG. 13. The amino acid sequence corresponding to positions 20–254 is set forth below:

Ser Thr Thr Ala Val Gln Thr Pro Thr Ser Gly Glu Pro Leu
Val Ser Thr Ser Glu Pro Leu Ser Ser Lys Met Tyr Thr Thr
Ser Ile Thr Ser Asp Pro Lys Ala Asp Ser Thr Gly Asp Gln
Thr Ser Ala Leu Pro Pro Ser Thr Ser Ile Asn Glu Gly Ser
Pro Leu Trp Thr Ser Ile Gly Ala Ser Thr Gly Ser Pro Leu
Pro Glu Pro Thr Thr Tyr Gln Glu Val Ser Ile Lys Met Ser
Ser Val Pro Gln Glu Thr Pro His Ala Thr Ser His Pro Ala
Val Pro Ile Thr Ala Asn Ser Leu Gly Ser His Thr Val Thr
Gly Gly Thr Ile Thr Thr Asn Ser Pro Glu Thr Ser Ser Arg
Thr Ser Gly Ala Pro Val Thr Thr Ala Ala Ser Ser Leu Glu
Thr Ser Arg Gly Thr Ser Gly Pro Pro Leu Thr Met Ala Thr
Val Ser Leu Glu Thr Ser Lys Gly Thr Ser Gly Pro Pro Val
Thr Met Ala Thr Asp Ser Leu Glu Thr Ser Thr Gly Thr Thr
Gly Pro Pro Val Thr Met Thr Thr Gly Ser Leu Glu Pro Ser
Ser Gly Ala Ser Gly Pro Gln Val Ser Ser Val Lys Leu Ser
Thr Met Met Ser Pro Thr Thr Ser Thr Asn Ala Ser Thr Val
Pro Phe Arg Asn Pro Asp Glu Asn Ser Arg Gly

As described above the anti-CD43 autoantibodies bind to forms of CD43 that possess less sialic acid than the form of CD43 found on the surface of normal T-lymphocytes. Anti-CD43 autoantibodies bind a form of CD43 from SupT1 cells that possess an apparent molecule weight of 120 kD, a form of CD43 from COS cells with an apparent molecular weight of 130kD, and a form of CD43 from normal thymocytes with an apparent molecular weight of 130 kD, all as determined by SDS-PAGE, as described above. COS cells and thymocytes produce more heavily sialated forms, with an apparent molecular weight of 120 kD, which are not bound by anti-CD43 autoantibodies.

A level of glycosylation that allows binding can be achieved by a number of conventional methods, e.g., by expressing the soluble CD43 fragment in an expression system that does not normally fully glycosylate foreign proteins (COS cells, as described above, produce a less glycosylated form (130 kD apparent molecular weight, as determined by SDS-PAGE) that is bound by anti-CD43 autoantibodies and a more glycosyalated form (120 kD apparent molecular weight, as determined by SDS PAGE) that is not), by expressing the soluble CD43 fragment in an expression system in which normal glycosylation is impaired, e.g., by the addition of an inhibitor, or by the enzymatic removal of sugar residues from a glycosylated soluble CD43 fragment. Sialic acid may be removed enzymatically, e.g., with neuraminadase (acylneuraminyl hydrolase, EC 3.2.1.18) e.g., neuroaminadase from *Vibrio cholerae* which hydrolizes α-2,3, α-2,4, α-2,6, and α-2,8 linked terminal sialic acid residues. Digestion of CD43 isolated from mature lymphocytes (from HIV-1 negative individuals) with *Vibrio cholerae* neuraminidase (Calbiochem) at 0.1 μ/ml for 45–60 minutes results in a degree of desialylation that allows anti-CD43 autoantibody binding.

Methods for the modification and removal of sugar groups found on glycoproteins are well known to those skilled in the art, see e.g., Bergh et. al. Patent Cooperation Treaty application WO8705330, hereby incorporated by reference.

The apparent molecular weight of a CD43 fragment that displays optimal binding to anti-CD43 autoantibodies will vary with the length of the fragment.

Hybrid Toxin Molecules

Cells with the potential to produce anti CD43 autoantibodies can be killed by hybrid toxin molecules, thereby preventing production of anti-CD43 autoantibodies and thus preventing this antibody from binding to lymphocytes and any other susceptible cells. Hybrid toxin molecules can be formed by coupling a cell specific ligand to one or more toxin molecules. The cell-specific ligand of a toxin molecule binds to a selected class of target cells and thus targets delivery of the toxin molecule to the target cell. Toxin molecule therapy would be adminstered prior to the appearence of anti-CD43 autoantibodies in HIV-1-infected individuals.

Hybrid toxins that bind to cells with the potential to produce anti-CD43 autoantibodies can be produced using a soluble CD43 antigen, e.g., a soluble CD43 fragment or a saccharide, as the cell-specific ligand. Suitable toxin molecules include bacterial and plant toxins e.g., diphtheria toxin or fragments thereof or ricin or fragments thereof; generally, the enzymatically active portion but not the generalized eukaryotic binding portion of the toxin is used.

When the cell specific-ligand and the toxin are peptides they may be coupled at the DNA level, i.e., they may be encoded by a single fused gene and expressed as a single polypeptide, by techniques well known to those skilled in the art, e.g. as described in Murphy U.S. Pat. No. 4,675,382, hereby incorporated by reference. The cell specific ligand and the toxin may be coupled at the protein level e.g., by covalently cross linking the cell specific ligand to the toxin by methods well known to those skilled in the art, e.g., as discussed in Bacha et al. U.S. Pat. No. 4,468,382, hereby incorporated by reference and in Greenfield et al. Patent Cooperation Treaty application WO85/03508, hereby incorporated by reference.

Preferred hybrid toxins include a soluble fragment of CD43 coupled by a peptide bond to a peptide toxin e.g., diphtheria toxin, encoded by a fusion gene. The construction and expression of such fusion genes are well known to those skilled in the art.

Therapeutic Use of Soluble CD43 Antigens

Soluble CD43 fragments will be admixed with a pharmaceutically acceptable carrier substance, e.g., saline, and administered, by a medically acceptable administration route, e.g., intravenously, intramuscularly, or orally, to patients infected with HIV, to inhibit the binding of anti-CD43 autoantibodies to cells, e.g., lymphocytes or brain cells, which carry CD43-like molecules on their surfaces.

The soluble CD43 fragments compete with CD43 on cell surfaces for anti-CD43 autoantibodies and thereby reduce the number of anti-CD43 autoantibodies available to bind to CD43 on cell surfaces. The binding of anti-CD43 to lymphocytes is believed to contribute to the course of disease in AIDS patients by, inter alia, marking the CD43 bearing lymphocytes for removal from circulating by the spleen. Administration of CD43 may also protect other cells, e.g., brain cells, from being bound by anti-CD43 autoantibodies.

The strategy described above consists essentially of supplying soluble protein fragments (soluble CD43) which bind to a molecule characteristic of the disease state (anti-CD43 autoantibodies) and thereby preventing the molecule characteristic of the disease state from interacting with a binding site (CD43 on the lymphocytes and other cells). This strategy is generally the same as that found in Reinberg et al., Patent Cooperation Treaty Application, WO 8903222, hereby incorporated by reference, Fisher et al., Australian Patent Application AU 38318/89-A1, hereby incorporated by reference, Anderson et al., U.S. patent application No. 7,234,646, hereby incorporated by reference, Mizakumi, U.S. patent application No. 7,344,304, hereby incorporated by reference, Capon et al., European Patent Application EP 314,317, hereby incorporated by reference, and Capon et al., Patent Cooperation Treaty Application Wo 8902922, hereby incorporated by reference, all of which describe the use of CD4 fragments to compete with the binding of the AIDS virus for binding cites on susceptible cells.

The amount of soluble CD43 administered will generally be between 10 micrograms/kg body weight and 500 micrograms/kg body weight per day, and will likely be administered as maintenance therapy for the life of a patient.

Anti-CD43 autoantibodies in healthy HIV-1 patients can be eliminated by immunizing the patient with CD43 antigen, e.g., desialylated CD43, and following this immunization by a course of therapy that kills dividing cells, e.g., a course of limited chemotherapy. The immunization will selectively activate B cells that make anti-CD43 antibodies and cause them to divide. Chemotherapy given at the time of cell division will preferentially kill the dividing cells. A similar course of treatment has been used to eliminate autoantibodies (known as circulating anti-coagulants) that bind to clotting factors and cause bleeding disorders. This form of therapy should be applied prior to the onset of immune deficiency.

Diagnostic Use of CD43 or CD43 Fragments

CD43, fragments thereof, or other CD43 antigens can be used in a standard immunoassay format for the detection of anti-CD43 autoantibodies (and thus the detection of HIV-1 infections and of CD4+ lymphocyte depletion) in serum or in eluates from lymphocytes. One standard format would involve coupling CD43, a fragment thereof, or another CD43 antigen to a solid support, e.g., standard beads, and contacting the immobilized CD43, CD43 fragments, or other CD43 antigens with a serum or lymphocyte eluate sample such that any anti-CD43 autoantibody in the sample will bind to the immobilized antigen. Subsequent incubation with anti-CD43 antibody, followed by standard detection steps, will indicate the presence or absence of anti-CD43 antibody in the sample.

Mechanism

CD43 has several features which suggest it plays a critical role in normal immune function. CD43 is expressed by essentially all leukocytes, Renold O'Donnell et al. (1987) Blood 70:104 and Borche et al. (1987) Eur. J. Immunol. 17:1523–1526, its expression is diminished or abnormal on lymphocytes from children with Wiskott-Aldrich syndrome, Renold O'Donnell et al. (1984) J. Exp Med. 157:1705–1723, a severe X chromosome-linked immunodeficiency, and binding antibody to CD43 can activate T lymphocytes, Mentzer et al. (1987) J. Exp. Med. 165:1383–1392 and Axelsson et al. (1988) J. Immunol. 141:2912–2917, by a mechanism independent from T cell receptor/CD3 complex mediated signaling, Silverman (1984) J. Immunol. 142:4194–4200. Moreover, binding of antibody to CD43 can induce homotypic adhesion by monocytes, Nong et al. (1989) J. Exp. Med. 170:259, and enhance NK mediated killing, Vargas-Cortes (1988) Scan. J. Immuno. 27:661. Taken together, these data support the notion that CD43 participates in antigen-independent signaling important for cellular immune responses. A CD43-like molecule has also been found on the surface of brain cells in rats, Losy et al. (1989) J. Neurocytol. 18:71–76.

Anti-CD43 autoantibodies are produced only by HIV-1-infected individuals. This may be due to the likelihood that in non infected individuals, non sialic acid epitopes of CD43 on circulating lymphocytes evade immunologic recognition because they are masked by sialic acid residues. However, in conditions where increased lymphocyte destruction is though to occur (e.g., HIV-1-induced lymphocyte cytopathicity), self immunogenic CD43 epitopes may be exposed. Autoantibodies that bind to a partially sialylated form of CD43 on normal human thymocytes could contribute to the severe thymic atrophy which accompanies AIDS.

Anti-CD43 autoantibodies may contribute to the pathology of AIDS by any or all of the following mechanisms: by binding CD43 or CD43-like molecules and thereby interferring with normal cell functions mediated by CD43 or CD43-like molecules; by contributing to the compliment dependent lysis of the cells targeted by anti-CD43 autoantibodies; or, by targeting anti-CD43 autoantibody bound lymphocytes for removal by the spleen.

Other Embodiments

Other embodiments are within the following claims. For example, any soluble CD43 fragment can be used in accordance with the therapeutic methods of the invention; it is only required that all or most of the transmembrane portion of CD43 is excluded, so that the fragment is soluble, that an appropriate amount of sialyc acid is present so that anti-CD43 antibodies produced by HIV-1 infected individuals will bind, and that the fragment is sufficiently long and sufficiently homologous to the natural molecule such that it can bind to the anti-CD43 antibodies found in HIV-1 infected individuals. The testing of a candidate fragment (or other candidate CD43 antigen) for the capacity to bind to an anti-CD43 antibody is a simple and routine matter. CD43 fragments can be generated at the DNA level, or by digestion of protein.

What is claimed is:

1. A method of treating a human patient infected with HIV-1 comprising administering to said patient a soluble CD43-antigen capable of binding to an anti-CD43 autoantibody produced by said patient, wherein said CD43-antigen is a soluble glycosylated CD43 fragment comprising an amino acid sequence homologous to amino acids 20-254 of CD43.

2. A method of making a recombinant soluble segment of CD43 consisting of amino acids 20-254 comprising culturing cells transformed by an expression vector comprising a DNA sequence encoding said soluble segment of CD43.

isolating said soluble segment of CD43 from said cells, and decreasing glycosylation of said isolated soluble segment of Cd43, if necessary, to promote binding thereof to anti-CD43 antibody.

3. The method of claim 2, wherein said soluble segment is the entirety of positions 20-245 of CD43.

4. A method of eliminating anti-CD43 antibodies in a healthy HIV-1 infected individual comprising, in the following order, immunizing said individual with a soluble segment of CD43 consisting of amino acids 20-254, and administering to said individual a treatment that kills dividing cells.

5. The method of claim 4 wherein said soluble segment of CD43 is the entirety of positions 20-245 of CD43.

* * * * *

UNITED STATES PATENT AND TRADEMARK OFFICE
CERTIFICATE OF CORRECTION

PATENT NO. : 5,252,556

DATED : October 12, 1993

INVENTOR(S) : Blair Ardman

It is certified that error appears in the above-indentified patent and that said Letters Patent is hereby corrected as shown below:

Column 2, line 1, replace "quence of CD43." with --peptide that includes a portion of the amino acid sequence of CD43.--;

Column 2, line 48, correct the spelling of "neuraminadase" to --neuraminidase--;

Column 3, line 1, before "negative individuals", add the following: --on CD43 isolated from mature lymphocytes of HIV-1--;

Column 4, line 2, replace "CD3$^{30}$" with --CD3$^{+}$--;

Column 4, line 40, replace "IG+" with --Ig$^{+}$--;

Column 5, line 6, replace "IG+" with --Ig$^{+}$--;

Column 5, line 8, replace "Ig" with --Ig$^{+}$--;

Column 5, line 22, replace "within" with --without--;

Column 6, line 9, replace "Hypague" with --Hypaque--;

Column 6, line 45, correct the spelling of "addition";

Column 10, line 34, replace "oat" with --goat--;

Column 10, line 57, replace "phenlymethysulfonyl-" with --phenylmethysulfonyl- --;

UNITED STATES PATENT AND TRADEMARK OFFICE
CERTIFICATE OF CORRECTION

PATENT NO. : 5,252,556

DATED : October 12, 1993

INVENTOR(S) : Blair Ardman

It is certified that error appears in the above-indentified patent and that said Letters Patent is hereby corrected as shown below:

Column 10, line 63, replace "aliguots" with --aliquots--;

Column 11, line 37, replace "interlukin" with --interleukin--;

Column 14, line 10, correct the spelling of "glycosylated";

Column 14, line 46, correct the spelling of "appearance";

Column 15, line 41, replace "7,234,646" with --07/234,646--;

Column 15, line 42, replace "7,344,304" with --07/344,304--;

Column 16, line 49, replace "though" with --thought--;

Column 18, claim 2, line 10, replace "Cd43" with --CD43--;

UNITED STATES PATENT AND TRADEMARK OFFICE
CERTIFICATE OF CORRECTION

PATENT NO. : 5,252,556

DATED : October 12, 1993

INVENTOR(S) : Blair Ardman

It is certified that error appears in the above-indentified patent and that said Letters Patent is hereby corrected as shown below:

Column 18, claim 3, line 13, after "soluble segment", add --of CD43--.

Signed and Sealed this

Thirty-first Day of May, 1994

Attest:

BRUCE LEHMAN

Attesting Officer

Commissioner of Patents and Trademarks